United States Patent [19]

Magolda et al.

[11] Patent Number: 5,110,831
[45] Date of Patent: May 5, 1992

[54] VINYLOGOUS HYDROXAMIC ACIDS AND DERIVATIVES THEREOF AS 5-LIPOXYGENASE INHIBITORS

[75] Inventors: Ronald L. Magolda, Wallingford, Pa.; Stephen W. Wright, Wilmington, Del.

[73] Assignee: Du Pont Merck Pharmaceutical Company, Wilmington, Del.

[21] Appl. No.: 621,152

[22] Filed: Nov. 30, 1990

[51] Int. Cl.$^5$ ............................................. A61K 31/135
[52] U.S. Cl. .................... 514/645; 514/336; 514/340; 514/351; 514/438; 514/444; 514/461; 514/575; 514/576; 514/578; 514/663; 514/825; 514/886; 546/329; 546/330; 549/59; 549/74; 549/472; 549/491; 558/411; 558/418; 560/64; 564/300; 564/301

[58] Field of Search ................ 564/301, 300; 514/645, 514/663, 575, 576, 578, 825, 886

[56] References Cited

PUBLICATIONS

Lin et al., J. of Heterocyclic Chem., 14, 345 (1977).
Furukawa et al., Chem. Pharm. Bull. 22(9) 1990–1995, (1974).
Summers et al., J. Med. Chem. 1987, 30, 2121–2128.

*Primary Examiner*—Richard L. Raymond
*Assistant Examiner*—S. Kumar

[57] ABSTRACT

The present invention relates to vinylogous hydroxamic acids, processes for their manufacture, pharmaceutical preparations containing them, and their use in the treatment of various disorders.

30 Claims, No Drawings

VINYLOGOUS HYDROXAMIC ACIDS AND DERIVATIVES THEREOF AS 5-LIPOXYGENASE INHIBITORS

BACKGROUND OF THE INVENTION

The present invention relates to vinylogous hydroxamic acids, processes for their manufacture, pharmaceutical preparations containing them, and their use in the treatment of various disorders.

Inflammatory diseases are a widespread cause of human suffering and loss of function. Additionally, the treatment of patients with these diseases represents a very large expense in terms of money, facilities and personnel. The incidence of many such diseases is expected to rise in the future as life expectancy and the median age of the population continue to increase.

Inflammatory diseases are known which affect many diverse tissues and organs in the body. Examples of diseases in which the inflammation is most apparent in the joints and related connective tissue are osteoarthritis, rheumatoid arthritis, tendonitis, bursitis, and the like. These diseases are most often treated with nonsteroidal anti-inflammatory agents such as aspirin, ibuprofen, and piroxicam, or with anti-inflammatory glucocorticosteroids. However, these treatments suffer either from a lack of efficacy in completely controlling the disease process, or from unacceptable toxic side effects.

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators of inflammation, the leukotrienes (LTs).

The naturally occurring leukotrienes derived from arachidonic acid are among the most potent in vivo regulators of biological activity known, showing their effects at sub-nanogram levels. They are released from many different cells, following immunologic or nonimmunologic stimulation. A wide variety of biological effects are associated with the leukotrienes. Unfortunately, many of these biological effects are associated with the painful symptoms of inflammatory diseases, including asthma, arthritis, and allergic reactions. The peptidic leukotrienes, represented by $LTC_4$, $LTD_4$, and $LTE_4$, are potent spasmogens, with 1000 times the activity of histamine. Inhaled $LTC_4$ causes the immediate development of symptoms resembling those of an asthmatic attack. $LTB_4$ and 5-HETE are potent chemotactic factors for inflammatory cells such as polymorphonuclear leukocytes. They have also been found in the synovial fluid of rheumatoid arthritis patients. Leukotrienes have also been implicated as important mediators in allergic rhinitis, psoriasis, adult respiratory distress syndrome, Crohn's disease, endotoxin shock, and ischemia induced by myocardial injury among others. British Medical Bulletin (1983), Vol. 39, No. 3, pp. 249–254, generally discusses the pharmacology and pathophysiology of leukotriene $B_4$. The biological activity of the LTs has been reviewed by Lewis and Austen (*J. Clinical Invest.*, 1984, 73, 889) and by Sirois (*Adv. Lipid Res.*, 1985, 21, 78). A compound capable of selectively inhibiting 5-lipoxygenase while having weaker inhibitory effects on the cyclooxygenase enzyme is beneficial by preventing the formation of inflammatory and bronchioconstrictor mediators while having little inhibitory effect on protective prostaglandins in the stomach or on the bronchodilatory cyclooxygenase products, for example. prostacyclin. This may therefore be of use in maintaining the integrity of the gastrointestinal mucosa.

Thus, lipoxygenase enzymes are believed to play an important role in the biosynthesis of mediators of asthma, allergy, arthritis, psoriasis, and inflammation. Blocking these enzymes interrupts the biochemical pathways believed to be involved in these disease states.

U.S. Pat. Nos. 4,769,461; 4,897,422; 4,623,661; 4,822,811 4,769,387 and 4,820,828; U.S. Patent application number 119,926 (Nov. 13, 1987) and European patent application number 0,279,263 (Aug. 24, 1988) disclose the anti-inflammatory activity and 5-lipoxygenase inhibitory activity of simple hydroxamic acids with the structure:

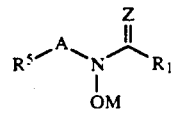

wherein A is a covalent bond or $C_1$ to $C_6$ alkylene or $C_2$ to $C_6$ alkenylene.

$R_1$ is H, $C_1$ to $C_4$ alkyl, $C_2$ to $C_4$ alkenyl, or $NR_2R_3$, wherein $R_2$ and $R_3$ are independently selected from H, $C_1$ to $C_4$ alkyl and hydroxyl, but $R_2$ and $R_3$ are not simultaneously hydroxyl.

X is O, S, $SO_2$, or $NR_4$, wherein $R_4$ is H, $C_1$ to $C_6$ alkyl, $C_1$ to $C_6$ alkoyl, or aroyl.

A is selected from $C_1$ to $C_6$ alkylene or $C_2$ to $C_6$ alkenylene.

n is 0 to 5.

Y is selected independently at each occurrence from H, halogen, OH, CN, halosubstituted alkyl, $C_1$ to $C_{12}$ alkyl, $C_2$ to $C_{12}$ alkenyl, $C_1$ to $C_{12}$ alkoxy, $C_3$ to $C_8$ cycloalkyl, aryl, aryloxy, aroyl, $C_1$ to $C_{12}$ aryalkyl, $C_1$ to $C_{12}$ arylalkenyl, $C_1$ to $C_{12}$ arylalkoxy, $C_1$ to $C_{12}$ arylthioalkoxy, and substituted derivatives for aryl, aryloxy, aroyl, $C_1$ to $C_{12}$ aryalkyl, $C_1$ to $C_{12}$ arylalkenyl, $C_1$ to $C_{12}$ arylalkoxy, $C_1$ to $C_{12}$ arylthioalkoxy, wherein substituents are selected from halo, nitro, cyano, $C_1$ to $C_{12}$ alkyl, alkoxy, and halosubstituted alkyl.

M is H, a pharmaceutically acceptable cation, aroyl, or $C_1$ to $C_{12}$ alkoyl.

$R_5$ is $R_1$ is phenyl [substituted 1 to 3 with Br, Cl, F, I, $CF_3$, alkyl $C_1$ to $C_{14}$, $NO_2$, CN, $OR_5$, CHO, $CH_2OR_5$, $CO_2R_5$, $COR_6$, phenyl, pyridyl (2, 3, 4), 2 or 3 thienyl, 2 or 3 furyl, $SO_3H$, $S(O)_oR_5$ (o=0 to 2), or $SO_2N(R_2)2$], naphthyl, 2, 3, or 4-pyridyl, 2 or 3 furyl, 2 or 3 thienyl, Y, alkyl ($C_1$ to $C_{14}$), or cycloalkyl of 3 to 6, trinuclear aromatic, or

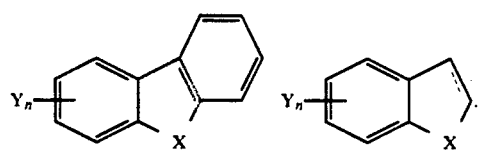

Compounds having these structures have also been described by Summers et al., *J. Med. Chem.*, 1987, 30, 2121; 1987, 30, 574; 1988, 31, 3; and 1988, 31, 1960; also by Huang et al., J. Med. Chem. 1989, 32, 1836; and by Jackson et al., J. Med. Chem. 1988, 31, 499.

U.S. Pat. Nos. 4,769,461 and 4,772,703 disclose the anti-inflammatory activity of simple hydroxamic acids with the structure:

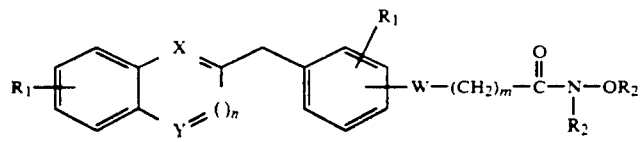

wherein W is a covalent bond, O, S, $NR_2$, CH(OH), C(O), or $NR_2C(O)$.

X is N or $CR_2$.

Y is O, S, $NR_2$, or $C(R_2)_2$ when n=0, or N or $CR_2$ when n=1.

Z is $CH_2O$, $CH_2S$, $CH_2N(R_2)$, O, S, $N(R_2)$, C(O), $C(O)NR_2$, $CH(R_2)CH(R_2)$, $C(R_2)=C(R_2)$, or $C\int C$.

$R_1$ is H, lower alkyl, $CF_3$, $NO_2$, OH, lower alkoxy, SH, lower alkylthio, or halogen.

$R_2$ is H or lower alkyl.

n is 0 to 1.

m is 1 to 6 with the proviso that m is 0 to 5 when W represents a covalent bond.

U.S. Pat. Nos. 4,761,403 and 4,757,078 disclose the anti-inflammatory activity and 5-lipoxygenase inhibitory activity of cyclic hydroxamic acids with the structure:

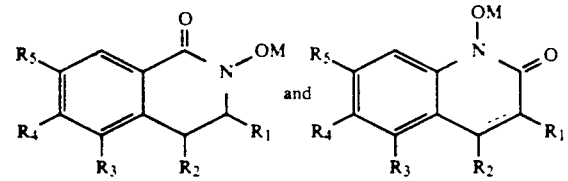

wherein $R_1$ through $R_5$ are independently selected from H, $C_1$ to $C_{12}$ alkyl, $C_1$ to $C_{12}$ alkoxy, $C_1$ to $C_8$ carbalkoxy, $C_6$ or $C_{12}$ aryl, $NO_2$, OH, halogen, or where $R_1$ to $R_2$, $R_3$ to $R_4$, or $R_4$ to $R_5$ form an aromatic fused ring.

M is a pharmaceutically acceptable cation, tri-$C_1$ to $C_6$-alkylsilyl or $C_1$ to $C_{12}$ alkyl or acyl.

Sarlo et al. describe the preparation and some reactions of 1-phenyl-2-phenyl-3-(N-hydroxy-N-phenyl)-2-propene-1-one in J. Chem. Soc. Perkin 1, 1978, 1113.

Padwa et al., J. Oro. Chem. 1986, 51, 3127, describe the synthesis and thermal cyclization reactions of

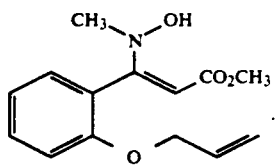

Woodward et al. describe the preparation of 1-phenyl-3-(N-hydroxy-N-phenyl)-2-propene-1-one and 1-(3'-hydroxysulfonyl)phenyl-2-phenyl-3-(N-hydroxy-N-phenyl)-2-propene-1-one in J. Oro. Chem., 1967, 14, 388.

Lang et al., J. Heterocyclic Chem., 1977, 14, 345, describe the synthesis of

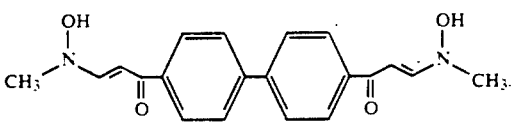

None of the above-described references disclose the compounds of the present invention or suggest that such compounds would possess activity as anti-inflammatory agents.

SUMMARY OF THE INVENTION

According to the present invention provided are compounds having the formula:

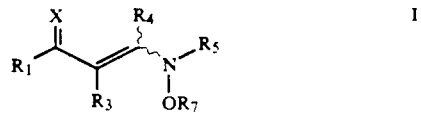

the sterioisomers and pharmaceutically acceptable salts thereof, wherein:

X is O or S;

$R_1$ is phenyl; phenyl optionally substituted with a total of 1 to 3 substituents each of which is !. independently selected from Br, Cl, F, I, CF3, $C_1$ to $C_{14}$ alkyl, $NO_2$, CN, $OR_5$, CHO, $CH_2OR_5$, $CO_2R_5$, $COR_6$, phenyl, 2, 3 or 4 pyridyl, 2 or 3 thienyl, 2 or 3 furyl, $SO_3H$, $S(O)_oR_5$ wherein o is 0 to 2, or $SO_2N(R_2)2$; naphthyl; 2, 3, or 4-pyridyl; 2 or 3 furyl; 2 or 3 thienyl; Y; $C_1$ to $C_{14}$ alkyl; or cycloalkyl of 3 to 6 carbon atoms;

Y is $OR_2$, $NR_2R_9$;

$R_2$ is H, $C_1$ to $C_4$ alkyl, or when Y is $NR_2R_9$ then $R_2$ and $R_9$ taken together can be $(Z)_m$ where m is 4 to 6 and Z is $CH_2$, O, S or $NR_{10}$, provided that no more than two of Z can be O, S or $NR_{10}$;

$R_3$ and $R_4$ independently represent H, $C_1$ to $C_4$ alkyl; phenyl; phenyl optionally substituted with 1 to 3 substituents each of which is independently selected from Br, Cl, F, I, $CF_3$, $C_1$ to $C_{14}$ alkyl, $NO_2$, CN, $OR_5$, CHO, $CH_2OR_5$, $CO_2R_5$, $COR_6$, phenyl, 2, 3 or 4 pyridyl, 2 or 3 thienyl, 2 or 3 furyl, $SO_3H$, $S(O)_oR_5$ wherein o is 0 to 2, or $SO_2N(R_2)_2$; naphthyl; 2, 3, or 4-pyridyl; 2 or 3 furyl, 2 or 3 thienyl; Y; $C_1$ to $C_{14}$ alkyl; cycloalkyl of 3 to 6 carbon atoms; or taken together may be $(Z)m$ where m=3 to 6;

$R_5$ is H, phenyl, benzyl, ($C_1$ to $C_6$ alkyl)phenyl, ($C_1$ to $C_6$ alkyl)heteroaryl wherein the heterocycle may be 2, 3, or 4-pyridyl, 2 or 3 furyl or 2 or 3 thienyl, naphthyl, $C_1$ to $C_{12}$ alkyl, or $C_3$ to $C_8$ cycloalkyl;

$R_6$ is H, phenyl, benzyl, ($C_1$ to $C_6$ alkyl)phenyl, ($C_1$ to $C_6$ alkyl)heteroaryl wherein the heterocycle may be 2, 3, or 4-pyridyl, 2 or 3 furyl or 2 or 3 thienyl, naphthyl, $C_1$ to $C_{12}$ alkyl, or $C_3$ to $C_8$ cycloalkyl;

$R_7$ is H, $R_8C(O)$, $R_8SO_2$, or a pharmaceutically acceptable cation;

$R_8$ is phenyl optionally substituted with a total of 1 to 3 substituents each of which is independently selected from Br, Cl, F, I, $CF_3$, $C_1$ to $C_{14}$ alkyl, $NO_2$, CN, $OR_5$, CHO, $CH_2OR_5$, $CO_2R_5$, $COR_6$, phenyl, 2, 3 or 4 pyridyl, 2 or 3 thienyl, or 2 or 3 furyl; naphthyl; 2, 3, or 4-pyridyl; 2 or 3 furyl; 2 or 3 thienyl; Y; $C_1$ to $C_{14}$ alkyl; or cycloalkyl of 3 to 6 carbon atoms;

$R_9$ is H, $C_1$ to $C_4$ alkyl, or when Y is $NR_2R_9$ then $R_2$ and $R_9$ taken together can be $(Z)_m$ where m is 4 to 6 and Z is $CH_2$, O, S or $NR_{10}$, provided that no more than two of Z can be O, S or $NR_{10}$;

$R_3$ and $R_1$ taken together can be $(Z)_m$ where m is 3 to 5 and Z is $CH_2$, O, S or $NR_{10}$, provided that no more than two of Z can be O, S or $NR_{10}$;

$R_3$ and $R_5$ taken together can be $(Z)_m$ where m is 2 to 4 and Z is $CH_2$, O, S or $NR_{10}$, provided that no more than two of Z can be O, S or $NR_{10}$;

$R_4$ and $R_5$ taken together can be $(Z)_m$ where m is 3 to 5 and Z is $CH_2$, O, S or $NR_{10}$, provided that no more than two of Z Can be O, S Or $NR_{10}$.

The compounds of Formula (I) are provided in the form of an individual stereoisomer, a non-racemic stereoisomer mixture, and a racemic mixture. Also provided are pharmaceutically acceptable salts of the compounds of Formula (I).

Also provided are pharmaceutical compositions containing compounds of Formula (I) and methods of using compounds of Formula (I) as anti-inflammatory agents.

Additionally provided are processes for preparing the compounds of Formula (I) as described hereinafter.

PREFERRED EMBODIMENTS

Preferred compounds are those compounds of Formula (I) as described above but wherein $R_7$ is H, $R_8C(O)$, or a pharmaceutically acceptable cation.

Most preferred compounds are those more preferred compounds wherein $R_3$ is not aryl.

Specifically preferred compounds are those more preferred compounds which are the following:

| | | |
|---|---|---|
| $R_1$ = 4-fluorophenyl; | X = O; | $R_3 = R_4 = R_7 = H$; |
| $R_5 = CH_3$; | | |
| $R_1$ = 4-fluorophenyl; | X = O; | $R_3 = R_4 = R_7 = H$; |
| $R_5 = CH_2C_6H_5$; | | |
| $R_1$ = 4-chlorophenyl; | X = O; | $R_3 = R_4 = R_7 = H$; |
| $R_5 = CH_3$; | | |
| $R_1$ = 4-chlorophenyl; | X = O; | $R_3 = R_4 = R_7 = H$; |
| $R_5 = CH_2C_6H_5$; | | |
| $R_1$ = 4-nitrophenyl; | X = O; | $R_3 = R_4 = R_7 = H$; |
| $R_5 = CH_3$; | | |
| $R_1$ = 4-nitrophenyl; | X = O; | $R_3 = R_4 = R_7 = H$; |
| $R_5 = CH_2C_6H_5$; | | |
| $R_1$ = 4-(phenyl)phenyl; | X = O; | $R_3 = R_4 = R_7 = H$; |
| $R_5 = CH_3$; | | |
| $R_1$ = 4-(phenyl)phenyl; | X = O; | $R_3 = R_4 = R_7 = H$; |
| $R_5 = CH_2C_6H_5$. | | |

Preferred compositions containing compounds of Formula (I) and methods of using compounds of Formula (I) as anti-inflammatory agents are those compositions and methods suitable for the treatment and prevention of disease states in which lipoxygenase may be involved, including, but not limited to, asthma, rheumatoid arthritis, gout, psoriasis, allergic rhinitis, adult respiratory distress syndrome, Crohn's disease, endotoxin shock, inflammatory bowel disease and/or ischemia induced myocardial or brain injury. In some cases this will involve preventing the underlying cause of the disease state and in other cases, while the underlying disease will not be affected the compounds of this invention will have the benefit of ameliorating the symptoms or preventing the manifestations of the disease.

DETAILED DESCRIPTION OF THE INVENTION

Synthesis

The compounds of Formula (I) can be prepared using the reactions and techniques described herein. The reactions are usually performed in a solvent appropriate to the reagents and materials employed, and suitable for the transformation being effected. In some cases functional groups on the starting materials may need to be protected by standard protecting groups reported in the chemical literature which are well known to one skilled in the art. In some cases, substituents on the starting materials may be incompatible with some of the reaction conditions required in some of the methods described. Such restrictions to the substituents which are compatible with the reaction conditions will be readily apparent to one skilled in the art and alternative methods described herein must then be used.

Many of the compounds of Formula (I) possess one or more chiral carbon atoms, allowing the occurrence of different enantiomers and/or diastereomers. In those cases where enantiomers are possible, the separate enantiomers may be obtained in pure or enantiomerically enriched form either by starting from a single enantiomer of a starting material (in those cases where the starting material also possesses the chiral carbon atom), or by resolution of the racemic mixture using standard methods. Diastereomers may generally also be separated using standard methods such as chromatography or fractional crystallization.

The compounds of Formula (I) may be converted to alkali addition salts by treatment with a suitable pharmaceutically acceptable alkali, using standard methods.

Several methods may be used to prepare the compounds of Formula (I). In Method A (Scheme 1), a ketone (II) may be reacted with a dialkylamide dialkylacetal, such as dimethylformamide dimethylacetal or dimethylacetamide dimethylacetal, to yield a vinylogous dimethylamide of structure (III). This reaction is usually conducted without solvent but may be conducted in a suitable organic solvent or solvent mixture such as tetrahydrofuran, dioxane, or N,N-dimethylformamide. The reactions are usually conducted at temperatures above room temperature, and frequently at the boiling point of the solvent. Examples of such preparations may be found in Ann. Chem. 1961, 641, 1 or J. Heterocyclic Chem., 1977, 14, 345. Alternative routes of preparation of compounds of type (III) are described in the chemical literature; for example, Chem. Berichte, 1930, 63, 1573, and Bull. Acad. Sci. USSR. Div. Chem. Sci., 1953, 991. The vinylogous amide (III) is then allowed to react with an appropriate hydroxylamine (IV), usually in the presence of a molar equivalent of acid. The reactions are usually conducted at room temperature, but may be carried out above room temperature. The reactions are usually conducted in water or a suitable organic solvent or solvent mixture such as methanol, ethanol, dichloromethane. Examples of suitable acids are hydrochloric, hydriodic, sulfuric, p-toluenesulfonic, or perchloric.

Many of the starting ketones for this method are known in the chemical literature, or may be prepared using known methods. The hydroxylamines for this method are known in the chemical literature, or may be prepared using known methods. Examples of known methods that are generally useful for the preparation of suitable ketones include the Friedel-Crafts reaction, the Hoesch reaction, the reaction of acyl halides with various organometallic reagents, the oxidation of suitable precursors such as secondary alcohols, olefins, and activated methylene groups, the hydrolysis of gem dihalides, and the decarboxylation of β-keto esters. Where $R_1$ and $R_3$ are joined in a ring, a cyclic ketone, such as cyclohexanone or α-tetralone, may be used as the starting material. Hydroxylamines of Formula (IV) may be prepared, for example, using methods disclosed by Borch, Bernstein, and Durst, *J. Am. Chem. Soc.*, 1971, 93, 2897 or Kawase and Kikugawa, *J. Chem. Soc.*, Perkin 1, 1979, 643. Method A is exemplified by the procedure of Example 1.

The following examples are provided to illustrate the preparation and use of the compounds described herein. The examples are provided for illustration only and are not to be construed as limiting the invention, either in spirit or scope, as modifications will be apparent from this disclosure to those skilled in the art.

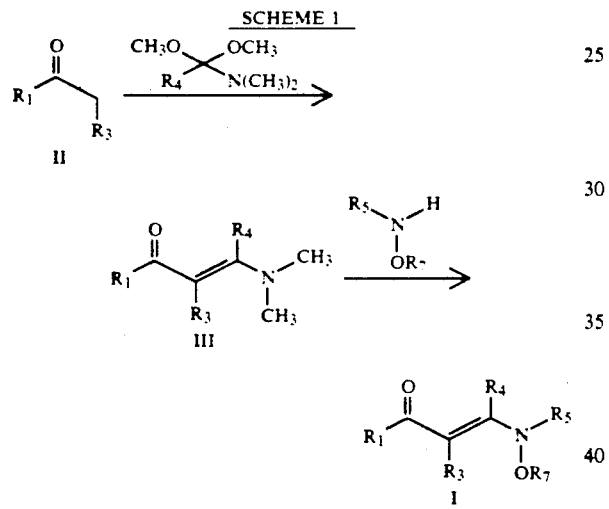

A second method (Method B) for preparing those compounds of Formula (I) is shown in Scheme 2. A ketone of Formula (II) may be converted to the b-ketoaldehyde or b-diketone derivative (V). This transformation is known as the Claisen condensation and is well known in the chemical literature, and may typically be performed using reagents such as ethyl or n-butyl formate in the presence of a basic reagent such as sodium methoxide, sodium ethoxide, potassium tert-butoxide or sodium hydride to form a β-ketoaldehyde, or an ester of the formula $R_4CO_2Et$ in the presence of a basic reagent such as sodium methoxide, sodium amide, potassium tert-butoxide or sodium hydride to form a β-diketone. A useful solvent for these reactions is tetrahydrofuran. The b-ketoaldehyde (V, $R_4=H$) or (-diketone (V, $R_4 \neq H$) may then be reacted with a hydroxylamine (IV) to give the compound of Formula (I). The latter reaction is usually conducted in a suitable organic solvent or solvent mixture such as methanol, ethanol, 2-propanol, or water. The reactions are usually conducted at temperatures below room temperature up to the boiling point of the solvent, preferably between about 0° and 0° C. Method B is exemplified by the procedure of Example 2.

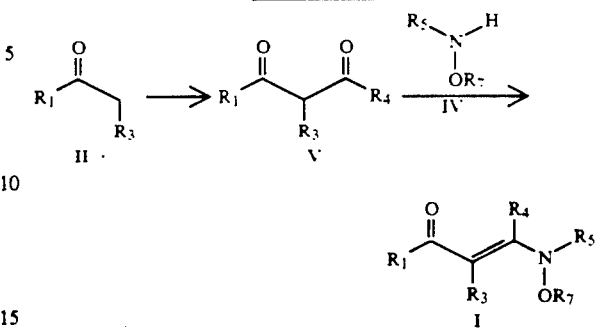

A third method (Method C) for preparing those compounds of Formula (I) is shown in Scheme 3. An acetylenic compound of Formula (VI) may be reacted with a hydroxylamine (IV) to provide the compound of Formula (I). The reactions are usually conducted in a suitable organic solvent or solvent mixture such as tetrahydrofuran, dioxane, methanol, or dichloromethane. The reactions are usually conducted at temperatures below room temperature up to the boiling point of the solvent, preferably between about 0° and 30° C. The starting materials for this method are known in the chemical literature, or may be prepared using known methods. Acetylenic compounds of Formula (VI) may be prepared, for example, using, for example, methods disclosed in *J. Org. Chem.*, 1977, 42, 3981, *J. Chem. Soc.*, 1937, 933, or *J. Am. Chem. Soc.*, 1967, 89, 5722. Method C is exemplified by the procedure of Example 3.

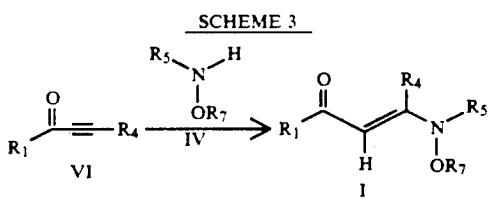

A fourth method (Method D) for preparing those compounds of Formula (I) is shown in Scheme 4. This method is especially useful for the preparation of those compounds of Formula (I) wherein $R_3$ and $R_4$ are joined in a ring. A β-dicarbonyl compound of Formula (VII) may be reacted with a hydroxylamine (IV) to provide the compound of Formula (I). The reactions are usually conducted in a suitable organic solvent or solvent mixture such as tetrahydrofuran, dioxane, methanol, or dichloromethane. The reactions are usually conducted at temperatures below room temperature up to the boiling point of the solvent, preferably between about 0° and 30° C. Suitable β-dicarbonyl starting materials are well known in the literature, or may be prepared by the Claisen condensation, the Dieckmann condensation, or by the acylation of enamines. Examples of such starting materials include 2-benzoylcyclohexanone and ethyl 2-cyclopentanonecarboxylate.

SCHEME 4

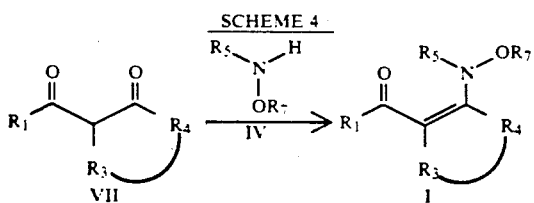

A fifth method (Method E) for preparing those compounds of Formula (I) is shown in Scheme 5. This method is especially useful for the preparation of those compounds of Formula (I) wherein $R_4$ and $R_5$ are joined in a ring. A β-dicarbonyl compound of Formula (VIII), where $R_4$ is, for example, methyl, may be converted to its dianion with two equivalents of a suitable base, such as lithium diisopropylamide, in an anhydrous solvent such as tetrahydrofuran, and the resultant dianion may then be allowed to react with a protected hydroxylamine, such as (IX), to provide the compound of Formula (X), which may be deprotected using standard methods to afford the compound of Formula (I) following spontaneous cyclization and dehydration. The synthesis and deprotection of protected hydroxylamines of Formula (IX) is described in *Tetrahedron Letters*, 1989, 30, 31.

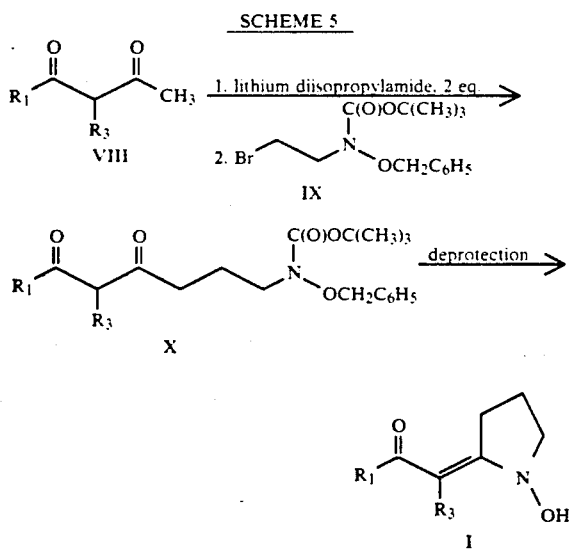

Certain substituents on $R_7$ in compounds of Formula (I) wherein $R_7$ is other than H may be prepared from other compounds of Formula (I) wherein $R_7$ is H by standard chemical manipulations which are well known to one skilled in the art. An example of the preparation of a compound of Formula (I) by functional group manipulation of another compound of Formula (I) is demonstrated by Example 4.

Examples of the preparation of vinylogous amide starting materials are given below. All temperatures are in degrees Celsius. All reactions are performed under an atmosphere of dry nitrogen. Concentration under reduced pressure is performed with a rotary evaporator using a water aspirator. All solutions were dried over anhydrous magnesium sulfate unless otherwise indicated. Nuclear magnetic resonance (NMR) spectra were obtained at a field strength of 200 or 300 mHz; abbreviations for NMR data are as follows: s=singlet, d=doublet, m=multiplet, $CDCl_3$=deuterochloroform solvent. Peak positions for NMR data are reported as parts per million downfield from the internal standard tetramethylsilane.

1-(2-naphthyl)-3-dimethylaminoprop-2-en-1-one

2'-Acetonaphthone (10 0 g, 58 mmol, [93-08-3]) was dissolved in 20 mL of N,N-dimethylformamide dimethylacetal [4637-24-5] and the mixture was heated under reflux for 14 hours. The mixture was then cooled, concentrated, and the crystalline residue was recrystallized from cyclohexane to give the title product as orange crystals (9.88 g, 76%). mp 100°–101°. Calc'd for $C_{15}H_{15}NO$: C 79.97%, H 6.71 %, N 6.22%; found: C 79.71%, H 6.76%, N 6.51%. NMR ($CDCl_3$): 8.40 (s, 1 H); 8.00–7.83 (m, 5 H); 7.54–7.51 (m, 2 H); 5.86 (d, 1 H); 3.33–2.83 (br d, 6 H). Mass spec 226 (M +H+).

1-(4-(Benzyloxy)phenyl)-3-dimethylaminoprop-2-en-1-one 4-(Benzyloxy)acetophenone (60.0 g, 0.265 mol, [54696-05-8]) was dissolved in 180 mL of N,N-dimethylformamide dimethylacetal and the mixture was heated under reflux for 48 hours. The mixture was then cooled, concentrated, and the crystalline residue was recrystallized from benzene in two crops to give the title product as yellow crystals (53.9 g, 72%). mp 138°. Calc'd for $C_{18}H_{19}NO_2$: C 76.84%, H 6.81%, N 4.98%; found: C 77.10%, H 6.58%, N 4.58%. NMR ($CDCl_3$): 7.89 (d, 2 H); 7.78 (d, 1 H); 7.47–7.32 (m, 5 H); 6.98 (d, 2 H); 5.70 (d, 1 H); 5.11 (s, 2 H), 3.33–2.83 (br d, 6 H). Mass spec 282 (M+H+).

1-(Cyclopropyl)-3-dimethylaminoprop-2-en-1-one

To a suspension of 5.94 g (0.11 mol) of sodium methoxide in 200 mL of dry THF was added 8.89 mL (0.11 mol) of ethyl formate, followed by methyl cyclopropyl ketone (9.91 mL, 0.10 mol, [765-43-5]). The reaction mixture rapidly turned yellow and was stirred at 25° for 4 hours. The reaction mixture was then concentrated and the residue was dissolved in 100 mL of methanol. To this was added a solution of 8.97 g (0.11 mol) of dimethylamine hydrochloride in 50 mL of methanol. The mixture was stirred for 1 hour at 25°, then the reaction mixture was concentrated. The residue was suspended in 100 mL of dry benzene and then concentrated. The residue was then triturated with 100 mL of dry benzene, filtered, and the filter cake was washed with additional dry benzene. The benzene solution was dried and concentrated to yield a yellow oil that crystallized upon cooling (11.97 g, 86%). mp 55°. NMR ($CDCl_3$): 7.58 (d, 1 H); 5.21 (d, 1 H); 3.20–2.60 (br d, 6 H); 1.80 (m, 1 H); 1.00 (m, 2 H); 0.77 (m, 2 H). Mass spec 140 (M+H+).

1-(4-Fluorophenyl)-3-dimethylaminoprop-2-en-1-one

4-Fluoroacetophenone (25 mL, 0.206 mol, [403-42-9]) and dimethylformamide dimethylacetal (72 mL) were combined and heated under reflux for 18 hours. The mixture was cooled and concentrated to yield a crystalline residue. This was triturated thoroughly with 40 mL of cyclohexane to yield the title product as orange crystals (28.8 g, 72%). mp 84°. Calc'd for $C_{11}H_{12}FNO$: C 68.38%, H 6.26%, N 7.25%; found: C 68.33%, H 6.22%, N 7.02%. NMR ($CDCl_3$): 8.04–7.82 (m, 3 H); 7.08 (t, 2 H); 5.71 (d, 1 H); 3.33–2.83 (br d, 6 H). Mass spec 193 (M+H+).

The preparation of the compounds of Formula (I) by Methods A through C is described in greater detail in Examples 1 to 3. In these examples, all temperatures are in degrees Celsius. All reactions are performed under an atmosphere of dry nitrogen. Concentration under reduced pressure is performed with a rotary evaporator using a water aspirator. All solutions were dried over anhydrous magnesium sulfate unless otherwise indicated. Chromatography refers to the method of medium-pressure column chromatography described by Still et al., *J. Org. Chem.*, 1978, 43, 2923. The composition of solvent mixtures used as chromatographic eluents are given in percentages by volume. Nuclear magnetic resonance (NMR) spectra were obtained at a field strength of 200 or 300 mHz; abbreviations for NMR data are as follows: s=singlet, d=doublet, dd=doublet of doublets, t=triplet, m=multiplet, CDCl$_3$=deuterochloroform solvent, DMSO-d6=deuterodimethylsulfoxide solvent, MeOH-d4=deuteromethanol solvent. Peak positions for NMR data are reported as parts per million downfield from the internal standard tetramethylsilane. Mass spectra were obtained using methane chemical ionization; data are reported as the ratio of charge to mass of the parent ion.

EXAMPLE 1a 1-(4-(Benzyloxy)phenyl)-3-(N-hydoxy-N-methyl)aminoprop-2-en-1-one A solution of 1-(4-(benzyloxy)phenyl)-3-dimethylaminoprop-2-en-1-one (5.63 g, 20 mmol) in 20 mL of dioxane and 80 mL of methanol was treated with a solution of 3.34 g (40 mmol) of N-methylhydroxylamine hydrochloride [4229- 44-1] in 10 mL of methanol. After 1 hour at 25°, the reaction mixture was chilled in ice. The yellow precipitate was filtered, washed with methanol, and dried to afford the title compound (4.31 g, 76%). mp 135° C. Calcd. for C$_{17}$H$_{17}$NO$_3$: C 72.07%, H 6.05%, N 4.94%; found: C 72.11%, H 5.77%, N 4.77%. NMR (9 CDCl$_3$: 1 CD$_3$OD) 7.99 (d 2 H); 7.78 (d, 1 H); 7.45-7.32 (m, 5 H); 7.04 (d, 2 H); 6.97 (d, 1 H); 5.15 (s, 2 H); 5.11 (s. 1 H); 3.78 (s, 3 H). Mass spec 284 (M+H$^-$), 268 (M +H$^+$ —O).

Selected compounds which were or may be prepared using the method of Example 1a are shown in Table 1.

TABLE 1

| Ex # | R$_1$ | X | R$_3$ | R$_4$ | R$_5$ | Yield | mp °C. |
|---|---|---|---|---|---|---|---|
| 1a | 4-BzOPh[1] | O | H | H | CH$_3$ | 76% | 135° |
| 1b | 2-Naphth[2] | O | H | H | CH(CH$_3$) (2-naphth) | 61% | 129° |
| 1c | 2-Naphth | O | H | H | c-C$_6$H$_{11}$ | 74% | 169° |
| 1d | 2-Naphth | O | H | H | CH$_3$ | 58% | 102° |
| 1e | c-C$_3$H$_5$ | O | H | H | 4-BzOPhCH$_2$ | 64% | 108° |
| 1f | 4-BzOPh | O | CH$_3$ | H | CH$_3$ | 36% | 104° |
| 1g | 4-PicOPh[3] | O | H | H | CH$_3$ | 82% | 131° |
| 1h | 4-FC$_6$H$_4$ | O | H | H | n-C$_{10}$H$_{21}$ | 18% | |
| 1i | 2-Benzthph[4] | O | H | H | CH$_3$ | 86% | 134° |
| 1j | c-C$_3$H$_5$ | O | H | H | CH$_2$(2-naphth) | 80% | 134° |
| 1k | c-C$_3$H$_5$ | O | H | H | CH$_2$C$_6$H$_4$-4-C$_6$H$_5$ | 72% | 131° |
| 1l | c-C$_3$H$_5$ | O | H | H | CH$_2$C$_6$H$_4$-4-OC$_6$H$_5$ | 81% | 100° |
| 1m | 4-CH$_3$OC$_6$H$_4$ | O | 4-CH$_3$OC$_6$H$_4$ | H | CH$_3$ | 10% | 184° |
| 1n | 4-CH$_3$SC$_6$H$_4$ | O | 4-FC$_6$H$_4$ | H | CH$_3$ | 11% | 222° |
| 1o | C$_6$H$_5$ | O | C$_6$H$_5$ | H | CH$_3$ | 9% | 164° |
| 1p | 4-FC$_6$H$_4$ | O | H | H | CH$_3$ | 20% | 81° |
| 1q | 4-O$_2$NC$_6$H$_4$ | O | H | H | CH$_3$ | 61% | 148° |
| 1r | 4-C$_6$H$_5$C$_6$H$_4$ | O | H | H | CH$_3$ | 65% | 145° |
| 1s | 4-CH$_3$OC$_6$H$_4$ | O | H | H | CH$_3$ | 44% | 114° |
| 1t | 4-ClC$_6$H$_4$ | O | H | H | CH$_3$ | 34% | 114° |

[1]4-Benzyloxyphenyl
[2]2-Naphthyl
[3]4-(4-Picolyloxyphenyl
[4]2-Benzothiophenyl

EXAMPLE 2a 1-(2-naphthyl)-3-(N-hydoxy-N-benzyl)aminoprop-2-en-1-one

A solution of 1-(2-naphthyl)-3-dimethylaminoprop-2-en-1-one (0.384 g, 2 mmol) in 5 mL of methanol was cooled in ice and a solution of 0.246 g (2 mmol) of N-benzylhydroxylamine [622-30-0] in 2 mL of methanol was added. Crystals began to separate after a brief time. After 1 hour at 0°, the mixture was filtered and the filter cake was washed and dried to give the title product as bright yellow crystals (0.484 g, 80%). mp 125°. Calc'd for C$_{20}$H$_{17}$NO$_2$: C 79.19%, H 5.65%, N 4.62%; found: C 78.99%, H 5.63%, N 4.41%. NMR (9 CDCl$_3$: 1 CD$_3$OD) 8.56, 8.35 (s, 1 H); 8.04-7.81 (m, 5 H); 7.66-7.29 (m, 7 H); 4.86, 3.66 (s, 2 H). Mass spec 304 (M+H$^+$), 288 (M+H$^+$-O).

Selected compounds which were or may be prepared using the method of Example 2a are shown in Table 2.

TABLE 2

| Ex. # | R$_1$ | X | R$_3$ | R$_4$ | R$_5$ | Yield | mp °C. |
|---|---|---|---|---|---|---|---|
| 2a | 2-Naphth[1] | O | H | H | CH$_2$C$_6$H$_5$ | 80% | 125° |
| 2b | 2-Naphth | O | H | H | C$_6$H$_5$ | 34% | 169° |
| 2c | 4-FC$_6$H$_4$ | O | H | H | CH$_2$C$_6$H$_5$ | 82% | 106° |
| 2d | 4-FC$_6$H$_4$ | O | H | H | c-C$_6$H$_{11}$ | 21% | 117° |
| 2e | 4-ClC$_6$H$_4$ | O | H | H | CH$_2$C$_6$H$_5$ | 74% | 120° |
| 2f | 4-PhC$_6$H$_4$ | O | H | H | CH$_2$C$_6$H$_5$ | 79% | 170° |

TABLE 2-continued

| Ex. # | R₁ | X | R₃ | R₄ | R₅ | Yield | mp °C. |
|---|---|---|---|---|---|---|---|
| 2g | 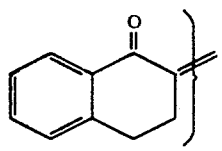 | | | H | CH₂C₆H₅ | 52% | 102° |

[1]2-Naphthyl

EXAMPLE 3a 3-(N-hydroxy-N-(4-benzyloxy)benzyl)aminobut-3-en-2-one

A solution of N-(4-benzyloxy)benzyl)hydroxyl-amine (0.250 g, 1 mmol) in 4 mL of dichloromethane was treated at 15° with 92 μL (1.2 mmol) of 3-butyn-2-one. The reaction mixture warmed, then slowly became yellow. The reaction mixture was kept 1 hour at 15°, then was concentrated and the residual foam was dissolved in 1-chlorobutane. The flask was stoppered and allowed to stand at 20° for 7 days. The white precipitate which formed was filtered and the residue remaining in the flask was triturated with 1-chlorobutane to give additional white powder. The material on the filter was washed with 1-chlorobutane, tert-butyl methyl ether and dried to give the title product as a buff colored powder (0.109 g, 37%). mp 115°–117°. Calc'd for $C_{18}H_{19}NO_3$: C 72.11%, H 6.44%, N 4.71%; found: C 72.75%, H 6.34%, N 4.69%. Mass spec 298 (M+H⁺), 282 (M+H⁺-O), 197 ($C_6H_5CH_2OC_6H_5CH_2^+$).

Selected compounds which were or may be prepared using the method of Example 3a are shown in Table 3.

TABLE 3

| Ex. # | R₁ | X | R₃ | R₄ | R₅ | Yield | mp °C. |
|---|---|---|---|---|---|---|---|
| 3a | CH₃ | O | H | H | CH₂C₆H₄-4-OCH₂C₆H₅ | 37% | 117° |
| 3b | OCH₃ | O | H | H | CH₂C₆H₄-4-OCH₂C₆H₅ | 63% | 121° |

An example of the preparation of compounds of Formula (I) by functional group manipulation of other compounds of Formula (I) is given in Example 4.

EXAMPLE 4

1-(4-(Benzyloxy)phenyl)-3-(N-acetoxy-N-methyl-)aminoprop-2-en-1-one

Four grams (14.1 mmol) of 1-(4-(benzyloxy)phenyl)-3-(N-hydoxy-N-methyl)aminoprop-2-en-1-one was suspended in 60 mL of dichloromethane at 20°. Acetic anhydride (1.46 mL, 15.5 mmol) was added and the mixture became homogeneous, after which triethylamine (2.55 mL, 18.3 mmol) was added. A transient orange color faded quickly and the mixture became yellow. The mixture was stirred at 20° for 30 minutes, then was concentrated and the residue was taken up in ether. The ethereal solution was washed with water, 1 M hydrochloric acid, water, 1 M sodium bicarbonate, brine, dried and evaporated. The remaining yellow oil was chromatographed on silica eluting with 1:1 hexane:ethyl acetate to give pure product that was crystallized from 1-chlorobutane:hexane to give the title product as a yellow powder (1.40 g, 31%). mp 61°. Calc'd for $C_{19}H_{19}NO_4$: C 70.14%, H 5.89%, N 4.31%; found: C 69.88%, H 5.83%, N 4.25%. NMR (CDCl₃): 7.91 (d, 2 H); 7.65 (d, 1 H); 7.48–7.32 (m, 5 H); 7.01 (d, 2 H); 6.03 (d, 1 H); 5.15 (s, 2 H); 3.30 (s, 3 H); 2.23 (s, 3 H). Mass spec 326 (M+H⁺), 268 (M+H⁺-CH₂=C=O).

UTILITY

The compounds of Formula (I) have been shown to inhibit the enzyme 5-lipoxygenase and to be efficacious in rodent models of inflammatory diseases. The potencies of the compounds as 5-lipoxygenase inhibitors were determined using a RBL-1 5-lipoxygenase assay. The procedure of Jakschik et al. was used (Jakschik, B. A.; Lee, L. H.; Shuffer, G.; Parker, C. W., *Prostaglandins*, 1978, 16, 733; Jakschik, B. A.; Sun, F. F.; Lee, L. H.; Steinhoff, M. M. *Biochem. Biophys. Res. Commun.*, 1980, 95, 100; Jakschik, B. A.; DiSantis, D. M.; Snakarappa, S. K.; Sprecher, H., *Biochem. Biophys. Res. Commun.*, 1981, 102, 624). The enzyme was prepared as a 10,000×g supernatant from homogenized RBL-1 cells. Because of variability in the enzyme content from culture to culture, an amount of supernatant was chosen to give a net production of 3300–3800 dpm of 5-HETE under the assay conditions (total cell protein 9–20 μg/assay). All reactions were run in duplicate. In a total volume of 100 μL, the appropriate amount of enzyme was incubated with test compound (prepared in 5% DMSO, 95% 0.2 M Tris, pH 8.5) in a phosphate buffer (45 mM sodium phosphate, 0.83 mM EDTA, 0.083% gelatin, 0.1 mM glutathione, 0.83 mM calcium chloride, 0.012 mM indomethacin) at pH 7.0 and 37° C. for 5 min. The reaction was initiated by the addition of 20 μL of a solution of arachidonic acid in phosphate buffer. The final concentration of substrate in the assay solution was 0.042 mM, including 0.167 μCi of [¹⁴C] arachidonic acid (specific activity 50 mCi/mmol). The reaction was terminated after 2 min by freezing in CO₂/ethanol. 5-LO products were separated from unreacted arachidonic acid on silica gel columns with hexane/ethyl acetate/acetic acid (82:17:1). 5-HETE was eluted with hexane/THF/ethyl acetate/acetic acid (65:30:10:1). Remaining products were eluted with methanol/water/acetic acid (70:30:1). Activity was measured as the total radioactivity in the 5-LO products, and inhibition was calculated at (1-D/C)×100%, where D is the activity in the presence of the test compound and C is the control activity. IC₅₀ values were calculated by linear regression analysis using three concentrations of drugs, spanning the 50% inhibition point. Results obtained in these models for selected compounds of Formula (I) are shown in Table 4.

TABLE 4

| Example | RBL-1 5-Lipoxygenase IC$_{50}$, μM |
|---|---|
| 1a | 1.6 |
| 1b | 2.2 |
| 1c | 2.5 |
| 1e | 3.1 |
| 1i | 0.44 |
| 1j | 1.5 |
| 1l | 1.4 |
| 1m | xx |
| 1q | 1.5 |
| 1r | 0.06 |
| 1s | 6.0 |
| 1t | 0.55 |
| 2a | 2.3 |
| 2b | 1.1 |
| 2c | 0.15 |
| 2d | 0.27 |
| 2e | 0.25 |
| 2f | 0.25 |
| 2g | 1.3 |
| 3a | 7.7 |

PHARMACEUTICAL COMPOSITIONS

The compounds of the invention can be administered to treat inflammation, including but not limited to rheumatoid arthritis, osteoarthritis, tendonitis, bursitis, psoriasis, contact dermatitis, eczema, inflammatory bowel disease, uveitis, and conjunctivitis, by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results. An ordinarily skilled physician or veterinarian can readily determine and prescribe an effective amount of the compound to prevent or arrest the progress of the condition.

Compositions (dosage forms) suitable for internal administration contain from about 1 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active ingredient usually contain suitable carriers, diluents, preservatives, or other excipients, as described in *Remington's Pharmaceutical Sciences*, Mack Publishing Co., a standard reference text in the field.

Gelatin capsules contain the active ingredient and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chloro-butanol.

The topical ointments, creams, gels, and pastes can contain diluents such as waxes, paraffins, starch, polyethylene glycol, silicones, bentonites, silicic acid, animal and vegetable fats, talc and zinc oxide or mixtures of these or other diluents. Topical solutions and emulsions can, for example, contain the customary diluents (with the exclusion of solvents having a molecular weight below 200 except in the presence of a surface-active agent), such as solvents, dissolving agents and emulsifiers; specific examples are water, ethanol, isopropanol, ethyl carbonate, benzyl alcohol, propylene glycol, oils, glycerol, and fatty acid esters of sorbitol or mixtures thereof. Compositions for topical dosing may also contain preservatives or anti-oxidizing agents.

Powders and sprays can contain the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active ingredient can be incorporated.

Patches can be made of a matrix such as polyacrylamide, and a semipermeable membrane made from a suitable polymer to control the rate at which the material is delivered to the skin.

Examples of useful pharmaceutical compositions for administration of the compounds of this invention can be illustrated as follows:

Capsules

A large number of unit capsules are prepared by filling standard two-piece hard gelatin capsules each with 50 mg of powdered active ingredient, 175 mg of lactose, 24 mg of talc, and 6 mg of magnesium stearate.

Soft Gelatin Capsules

A mixture of active ingredient in soybean oil is prepared and injected by means of a positive displacement pump into gelatin to form soft gelatin capsules containing 50 mg of the active ingredient. The capsules are washed in petroleum ether and dried.

Tablets

A large number of tablets are prepared by conventional procedures so that the dosage unit is 50 mg of active ingredient, 6 mg of magnesium stearate, 70 mg of microcrystalline cellulose, 11 mg of cornstarch, and 225 mg of lactose. Appropriate coatings may be applied to increase palatability or delay absorption.

Suspension

An aqueous suspension is prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection is prepared by stirring 1 5% by weight of active ingredient in 10% by volume propylene glycol and water. The solution is sterilized by commonly used techniques.

Nasal Spray

An aqueous solution is prepared such that each 1 mL contains 10 mg of active ingredient, 1.8 mg methylparaben, 0.2 mg propyl-paraben and 10 mg methylcellulose. The solution is dispensed into 1 mL vials.

Lung Inhaler

A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

Ointment

The active ingredient is added to a mixture of 48% by weight white petrolatum, 10% liquid petrolatum, 8% glycerol monostearate, 3% isopropyl myristate, and 20% lanolin at 70° C. After thorough mixing, a warm solution of methyl and propyl parabens in water containing sodium acetone bisulfite is added such that the final concentrations of each paraben is 0.15%, of water is 8%, and of sodium acetone bisulfite is 0.5%. The mixture is stirred until it has reached room temperature.

What is claimed is:

1. A compound having the formula:

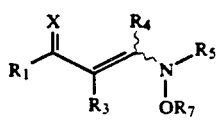

the sterioisomers and pharmaceutically acceptable salts thereof, wherein:

X is O;

$R_1$ is phenyl; phenyl optionally substituted with a total of 1 to 3 substituents each of which is independently selected from Br, Cl, F, I, $CF_3$, $C_1$ to $C_{14}$ alkyl, $NO_2$, phenyl naphthyl, $C_1$ to $C_{14}$ alkyl; or cycloalkyl of 3 to 6 carbon atoms;

$R_3$ and $R_4$ independently represent H, $C_1$ to $C_4$ alkyl; phenyl; phenyl optionally substituted with 1 to 3 substituents each of which is independently selected from Br, Cl, F, I, $CF_3$, $C_1$ to $C_{14}$ alkyl, $NO_2$, phenyl, naphthyl, $C_1$ to $C_{14}$ alkyl, cycloalkyl of 3 to 6 carbon atoms;

$R_5$ is H, phenyl, benzyl, ($C_1$ to $C_6$ alkyl)phenyl, naphthyl, $C_1$ to $C_{12}$ alkyl, or $C_3$ to $C_8$ cycloalkyl;

$R_7$ is H, or a pharmaceutically acceptable cation;

2. A compound of the formula

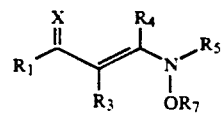

and pharmaceutically acceptable salts thereof wherein $R_1$ is lower alkyl, lower alkoxy, phenyl, $4\text{-}O_2NC_6H_4$, $4\text{-}ClC_6H_4$ or $Ph\ C_6H_4$;

$R_3$ is hydrogen, lower alkyl, phenyl, or $4\text{-}FC_6H_4$;

$R_4$ is hydrogen;

$R_5$ is lower alkyl, phenyl, benzyl, $n\text{-}C_{10}H_{21}$, $c\text{-}C_6H_{11}$, $CH_2$ (2-naphthyl), $CH(CH_3)$(2-naphthyl) or $CH_2C_6H_4\text{-}4\text{-}C_6H_5$; and X is O.

3. A compound of the formula

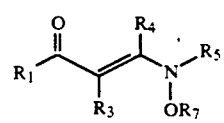

and pharmaceutically acceptable salts thereof wherein $R_1$ is 4-chlorophenyl, 4-fluorophenyl, 4-nitrophenyl or 4-(phenyl)phenyl;

$R_3$, $R_4$ and $R_7$ are each hydrogen; and $R_5$ is $CH_3$ or $CH_2C_6H_5$.

4. The compound of claim 3 wherein $R_1$ is 4-fluorophenyl;

$R_3$, $R_4$ and $R_7$ are each hydrogen; and $R_5$ is $CH_3$.

5. The compound of claim 3 wherein $R_1$ is 4-fluorophenyl;

$R_3$, $R_4$ and $R_7$ are each hydrogen; and $R_5$ is $CH_2C_6H_5$.

6. The compound of claim 3 wherein $R_1$ is 4-chlorophenyl;

$R_3$, $R_4$ and $R_7$ are each hydrogen; and $R_5$ is $CH_3$.

7. The compound of claim 3 wherein $R_1$ is 4-chlorophenyl;

$R_3$, $R_4$ and $R_7$ are each hydrogen; and $R_5$ is $CH_2C_6H_5$.

8. The compound of claim 3 wherein $R_1$ is 4-nitrophenyl;

$R_3$, $R_4$ and $R_7$ are each hydrogen; and $R_5$ is $CH_3$.

9. The compound of claim 3 wherein $R_1$ is 4-nitrophenyl;

$R_3$, $R_4$ and $R_7$ are each hydrogen; and $R_5$ is $CH_2C_6H_5$.

10. The compound of claim 3 wherein $R_1$ is 4-(phenyl)phenyl;

$R_3$, $R_4$ and $R_7$ are each hydrogen: and $R_5$ is $CH_3$.

11. The compound of claim 3 wherein $R_1$ is 4-(phenyl)phenyl;

$R_3$, $R_4$ and $R_7$ are each hydrogen: and $R_5$ is $CH_2C_6H_5$.

12. A pharmaceutical composition comprising a therapeutically effective amount of a compound of claim 1 and a pharmaceutically acceptable carrier.

13. A pharmaceutical composition comprising a therapeutically effective amount of a compound of claim 2 and a pharmaceutically acceptable carrier.

14. A pharmaceutical composition comprising a therapeutically effective amount of a compound of claim and a pharmaceutically acceptable carrier.

15. The pharmaceutical composition of claim 14 wherein $R_1$ is 4-chlorophenyl;

$R_3$, $R_4$ and $R_7$ are each hydrogen; and $R_5$ is $CH_2C_6H_5$.

16. The pharmaceutical composition of claim 13 wherein $R_1$ is 4-nitrophenyl;

$R_3$, $R_4$ and $R_7$ are each hydrogen; and $R_5$ is $CH_3$.

17. The pharmaceutical composition of claim 13 wherein $R_1$ is 4-nitrophenyl;

$R_3$, $R_4$ and $R_7$ are each hydrogen: and $R_5$ is $CH_2C_6H_5$.

18. The pharmaceutical composition of claim 13 wherein $R_1$ is 4-(phenyl)phenyl;

$R_3$, $R_4$ and $R_7$ are each hydrogen: and $R_5$ is $CH_3$.

19. The pharmaceutical composition of claim 13 wherein $R_1$ is 4-(phenyl)phenyl;

$R_3$, $R_4$ and $R_7$ are each hydrogen; and $R_5$ is $CH_2C_6H_5$.

20. A method of treating leukotriene mediated diseases comprising administering to a mammal in need of such treatment a therapeutically effective leukotriene antagonistic amount of a compound of claim 1.

21. A method of treating inflammatory diseases comprising administering to a mammal in need of such treatment a therapeutically effective anti-inflammatory amount of a compound of claim 1.

22. A method of treating inflammatory diseases comprising administering to a mammal in need of such treatment a therapeutically effective anti-inflammatory amount of a compound of claim 2.

23. A method of treating inflammatory diseases comprising administering to a mammal in need of such treatment a therapeutically effective anti-inflammatory amount of a compound of claim 3.

24. A method according to claim 21 wherein the inflammatory disease is rheumatoid arthritis.

25. A method according to claim 21 wherein the inflammatory disease is psoriasis.

26. The method according to claim 23 wherein in the compound $R_1$ is chlorophenyl;

$R_3$, $R_4$ and $R_7$ are each hydrogen; and $R_5$ is $CH_2C_6H$.

27. The method according to claim 23 wherein in the compound $R_1$ is 4-nitrophenyl;

$R_3$, $R_4$ and $R_7$ are each hydrogen; and $R_5$ is $CH_3$.

28. The method according to claim 23 wherein in the compound $R_1$ is 4-nitrophenyl;

$R_3$, $R_4$ and $R_7$ are each hydrogen; and $R_5$ is $CH_2C_6H$.

29. The method according to claim 23 wherein in the compound $R_1$ is 4-(phenyl)phenyl;

$R_3$, $R_4$ and $R_7$ are each hydrogen; and $R_5$ is $CH_3$.

30. The method according to claim 23 wherein in the compound $R_1$ is 4-(phenyl)phenyl;

$R_3$, $R_4$ and $R_7$ are each hydrogen; and $R_5$ is $CH_2C_6H$.

* * * * *